United States Patent [19]

Ranade

[11] Patent Number: 4,803,076
[45] Date of Patent: Feb. 7, 1989

[54] CONTROLLED RELEASE DEVICE FOR AN ACTIVE SUBSTANCE

[75] Inventor: Gautam R. Ranade, East Lyme, Conn.

[73] Assignee: Pfizer Inc., New York, N.Y.

[21] Appl. No.: 904,070

[22] Filed: Sep. 4, 1986

[51] Int. Cl.⁴ .................... A23K 1/18; A01N 29/04; A61K 31/025; A61K 31/03
[52] U.S. Cl. .................... 424/438; 424/468; 424/475; 424/486; 425/352; 425/353
[58] Field of Search ............ 424/438, 468, 475, 486, 424/487; 427/3; 604/890, 892; 425/352, 353

[56] References Cited

U.S. PATENT DOCUMENTS

| | | | |
|---|---|---|---|
| 2,987,445 | 6/1961 | Levesque | 167/82 |
| 3,113,076 | 12/1963 | Jacobs | 167/82 |
| 3,146,169 | 8/1964 | Stephenson et al. | 167/82 |
| 3,279,996 | 10/1966 | Long et al. | 167/82 |
| 3,851,648 | 12/1974 | Brooke | 604/892 |
| 4,044,119 | 8/1977 | Carlson et al. | 424/438 |
| 4,220,152 | 9/1980 | Dresback | 604/892 |
| 4,553,973 | 11/1985 | Edgren | 427/3 X |
| 4,601,893 | 7/1986 | Cardinal | 604/892 X |
| 4,642,230 | 2/1987 | Whitehead et al. | 424/438 X |

FOREIGN PATENT DOCUMENTS 972128 10/1964 United Kingdom ............... 424/438
2077103 12/1981 United Kingdom .

OTHER PUBLICATIONS

Brooke et al., J. Pharm. Sci. 66, pp. 159–162, 1977.
Lipper et al., J. Pharm. Sci. 66, pp. 163–164, 1977.
Langer et al., A. I. Chem. Engineers, Symposium Series, No. 206, vol. 77, pp. 10–20, 1981.
Hsieh et al., J. Pharm. Sci. 72, pp. 17–22, 1983.
Lai et al., Abstract No. 133, A.Ph.A. Meeting, Oct. 21–24, 1985.
Promotional Literature re Markham 156AMkIII Tablet/Capsule Printer, Markham Corp., Keene, N.H., Mar. 1985.

Primary Examiner—Michael Lusignan
Attorney, Agent, or Firm—Peter C. Richardson; J. Trevor Lumb; Robert K. Blackwood

[57] ABSTRACT

A device for the controlled release of a substance having useful activity into a fluid medium at a substantially constant rate, said substance contained in a shape which is substantially that of a truncated cone by means of an impermeable wall or coating on the base and side (but not the top) of said truncated cone. Apparatus useful in manufacture when said device is a tablet for administration to a mammal.

39 Claims, 11 Drawing Sheets

CONTROLLED RELEASE DEVICE FOR AN ACTIVE SUBSTANCE

BACKGROUND OF THE INVENTION

The present invention is broadly directed to a device for the controlled release of an active substance into a fluid medium at a substantially constant (i.e., zero-order) rate over an appreciable or prolonged time interval. Said device comprises said substance homogeneously disposed and contained substantially in the shape of a truncated cone by means of an impermeable wall or coating on the base and side (but not the top) of said cone. When the device is a partially coated tablet, particularly a tablet comprising a pharmaceutically effective agent for oral use in a mammal, the present invention is also directed to a tablet press for use in the manufacture of a tablet substantially in the shape of said truncated cone, and (after fully coating such tablets by conventional means) to an apparatus for removal of the tablet coating from the top (i.e., smaller diameter end) of the tablets.

A readily manufactured device which will dependably release an active material (e.g., a pharmaceutical agent, a cleanser or a deodorizer) at a zero-order rate into a fluid medium (gaseous or liquid) has remained an elusive goal, particularly when the device is in the form of a tablet for controlled in vivo release of a pharmaceutical agent into a biological fluid (e.g., the fluid of the gastrointestinal tract).

An early proposed method was that of Jacobs, U.S. Pat. No. 3,113,076 (1963) in which the drug was combined in a suitable carrier and tablets obtained by an extrusion method. The principle was to form tablets with approximately equal outer and "inner" surfaces, the latter accessed by aperture(s). As the exterior surface is dissolved, the area decreases, while as the inner surface dissolves, the surface area increases. Absent diffusion effects respecting the interior surface, the total surface, and thus rate of solution, would remain relatively constant. In its simplest form, Jacobs' tablet is a cylinder achieving equal inner surface by a multiplicity of cylindrical holes which are parallel to the axis of the outer cylinder, and accessed by the multiple apertures at each end of the cylinder. A related, but more sophisticated device, which now takes into account diffusion effects with respect to the inner surfaces, is that of Brooke, U.S. Pat. No. 3,851,648 (1974). Brooke discloses a cylindrical container, closed at the ends, with a cavity in the shape of a cylinder sector with the aperture in the form of a slot in the outer surface of cylinder (parallel to the axis of the cylinder), said slot at the apex of the cylinder sector cavity. See also Brooke et al., J. Pharm. Sci. 66, pp. 159-162 (1977). In practice, this device produces release rates which are initially high; Lipper et al., J. Pharm. Sci. 66, pp. 163-164 (1977). It is suggested that the device might be implanted into body cavities, but there is no suggestion for use of this device in the form of an ordinary tablet, or for a method of manufacturing such a tablet.

Langer et al., A.I.Ch.E. Symposium Series, No. 206, vol. 77, pp. 10-20 (1981) analyzed several geometries for approaching zero-order release kinetics; a slab (open in one of its major faces; a coated half-cylinder with a parallel, half-cylinder opening in its flat face; and a coated hemisphere with a small, open concavity in the center of its flat face. Only the latter provides predicted release rates close to zero-order, although even here an initially faster release is predicted, a result shown in practice by Hsieh et al., J. Pharm. Sci. 72, pp. 17-22 (1983) for release of sodium salicylate. Hsieh et al. propose a method for fabrication of such hemispheric devices in tablet form by initially molding a mixture of the drug and polymeric carrier, inserting a stick or bead into the center of the flat face, coating and finally removing the stick or bead from the face to form the small concavity. Such a method is hardly amenable to high speed tablet manufacture. Even without such methods, major problems were encountered by Hsieh et al. in this fabrication method, both in the techniques of coating and in uniformly opening the cavity.

Various types of boluses, for the relatively long term release of an active agent in the rumen or reticulum of a ruminant mammal, based on designs similar to those for tablets as discussed above, are also found in the prior art. See, for example, Dresback, U.S. Pat. No. 4,220,152 (1980), Cardinal, U.S. Pat. No. 4,601,893 (1986) and Guerrero et al., U.K. Patent Appln. No. 2,077,103 (1980).

More recently, Lai et al., Abstract No. 133, A.Ph.A. Meeting, Oct. 21-24, 1985, derived mathematical diffusional models for drug release from various geometries including "a hemisphere with a dimple-shaped releasing surface" (presumably as described above) and "a truncated cone and a tapered cylinder with central releasing hole". No actual or suggested preparation of such tablets is indicated, nor is any possible advantage suggested for the truncated cone over the coated hemisphere described above.

SUMMARY OF THE INVENTION

We have now discovered a device for the controlled release of active substance into a fluid medium at a substantially constant (i.e., zero-order) rate which comprises said substance homogeneously disposed, with or without one or more inert diluents, and contained substantially in the shape of a truncated cone by means of an impermeable wall or coating on the base and side of said truncated cone. In a first preferred embodiment, the truncated cone has top to bottom (base) diameters in a ratio of 1:2 to 1:4 and a height to base diameter in a ratio of 1:1 to 1:4. In a second preferred embodiment, the cone has a convex base, which minimizes any tailing effect in which there is slower release of the active product at the end of the release period. Optionally the sides of the cone, when viewed in cross-section, are concave in shape. The expression "substantially truncated cone" is intended to encompass not only a true truncated cone (alternatively called the frustum of a cone), but variants possessing said convex base, said concave sides, a small disc or flat cylindrical section at the base of the cone, and/or an oval or polygonal cross-section in place of the circular cross-section of the cone. The term "fluid" is intended to encompass either liquid or gaseous media. The expression "impermeable wall or coating" encompasses any material which prevents any substantial movement of the contents or of the surrounding fluid across the wall or coating.

Preferred embodiments of the present invention include a device wherein the substance or substances released are biologically active, such as an odor reducing, antimicrobial (germicidal) or pharmaceutical substance.

In one of its more preferred embodiment, the device is a tablet for oral administration to a mammal, which releases a pharmaceutically active substance into the fluid of the gastrointestinal tract of said mammal at a substantially constant rate over an appreciable time interval. Such pharmaceutically active substances include, but are not restricted to, analgesics, anorexics, anthelmintics, antibacterials, antifungals, antidepressants, antihypertensives, bronchodilators, immunosuppressants, antiinflammatories and blood glucose lowering agents. The active substance is usually combined with inert ingredients, to aid in tablet formation, and/or in controlling the rate of release of said active ingredient. For example, the excipients will permit high speed tabletting by means of a tablet press which has been modified with an upper punch having a cavity which is substantially in the shape of a truncated cone, also a part of the present invention. Such tablets are coated with a material substantially impermeable to the tablet contents and to gastrointestinal fluids, using methods well known in the art. Finally, the impermeable coating is removed from the top of each cone shaped tablet, employing special apparatus which is also part of the present invention.

The inert ingredients employed in tablets can be of the dissolution type (i.e., eroding and generally dissolving at the same time as the active ingredient), or they can form a matrix which is not soluble, and retains its shape as the active ingredient dissolves. When the inert ingredients are of the dissolution type, the coating should be relatively rigid so as to retain its shape as the tablet contents dissolve away into the fluid of the gastrointestinal tract.

In its most preferred embodiments, the present invention is directed to tablets in which the pharmaceutically active substance is an antihypertensive (particularly prazosin, trimazosin or doxazosin), an antianxiety agent (particularly hydroxyzine), a bronchodilator (particularly pirbuterol) or a blood-glucose lowering agent (particularly glipizide).

In another more preferred embodiment, the present invention is directed to a bolus for retention in the rumen or reticulum (i.e., the rumeno-reticular sac) in longer term treatment of ruminants. The bolus is of a weight or shape so as to be retained in the rumen for at least two weeks, and so as to be readily administered by means of a conventional bolling gun.

Representative of the drugs which can be used individually or in combination in the bolus devices described herein are the following: anthelmintics, including morantel, pyrantel, oxantel, piperazine, diethylcarbamazine, levamisole, tetramisole, and hygromycin B; antibacterials including sulfa drugs such as sulfanilamide, sulfathiazole, sulfamethazine, sulfaguanidine, and sulfapyridine; tetracyclines, such as 5-oxytetracycline, chlorotetracycline, doxycycline and Mannich bases thereof; penicillins such as ampicillin, penicillin G; aminoglycosides such as neomycin, streptomycin, apramycin, bacitracin as its zinc or methyl disalicyclic acid derivative; macrolides such as erythromycin, oleandomycin and tylosin; antibacterial growth promotants such as avoparicin, polymyxin, lincomycin, bambermycin and efrotomycin; hormonal growth promotants including diethylstilbestrol, zearalanol and melengestrol acetate; antiparasitic parasitic agents such as amprolium; nutritional agents such as salts of magnesium, selenium, copper and vitamins such as thiamine hydrochloride; molluscicides such as N-tritylmorphine; and bloat prevention agents such as alcohol ethoxylates and poly(oxyethylene)poly(oxypropylene)-poly(oxyethylene)polymers, e.g. poloxalene.

DETAILED DESCRIPTION OF THE INVENTION

The present invention is readily practiced, offering advantages over controlled release devices previously available. One advantage is the nearly constant (zero order) rate of release of active ingredient over virtually the entire release period, particularly when the base of the present truncated cone is convex in shape. Another advantage is the eas of manufacture, particularly in the case of tablets containing pharmaceutically active agents for use in mammals, where the present invention further provides apparatus useful in the manufacture of such tablets.

Figure 4:
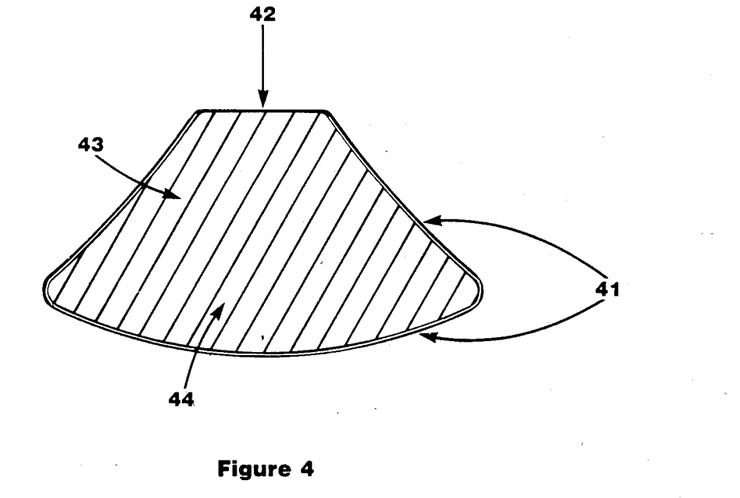
FIG. 4 illustrates in cross-section a tablet or container of the present invention with preferred convex base and optional concave sides.

When the device is macro in nature, such as a device for slow release of a deodorizer into a room or of an antimicrobial agent and/or a deodorizer into a toilet tank, the wall can be constructed as a container from standard construction materials, such as a moldable plastic, using methods standard in the art. The preconstructed container can then be filled with the active agent, usually in an inert carrier. Such a device is illustrated in FIG. 4, in cross-section, having an impermeable wall 41 on the convex bottom 44 and concave side 43, access of the contents to the fluid environment at the top 42 of the truncated cone, and contents substantially in the shape of a truncated cone.

When the present device is a tablet, ordinary cylindrical or drum shaped tablets containing the desired active ingredient and excipients can be formed on a conventional tablet press, then ground or filed to produce tablets of the desired truncated cone shape, hand coated and the coating removed from the top of the truncated cone with a razor blade. However, the present invention further provides apparatus for the much more highly efficient manufacture of such tablets.

Figure 1:
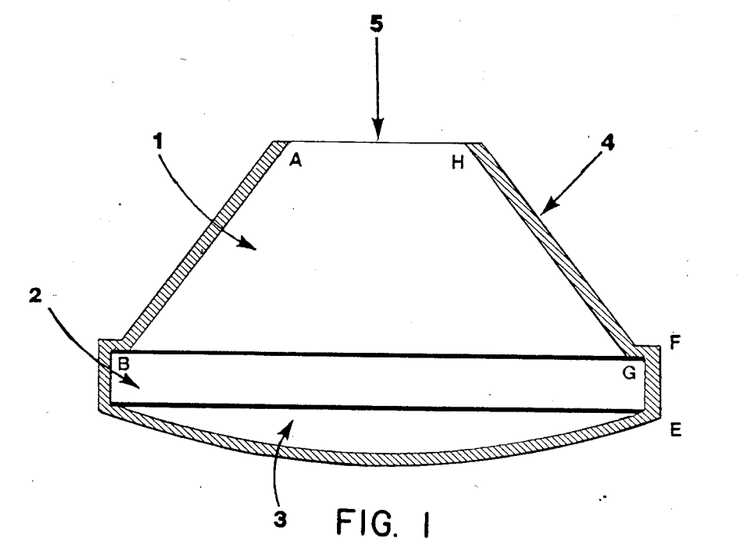
FIG. 1 shows in cross-section a view of a tablet of the present invention, prepared on a conventional tabletting machine using the punches of the present invention, then coated and the coating at the top of the cone removed by means of the coating removal apparatus of the present invention.
Figure 5:
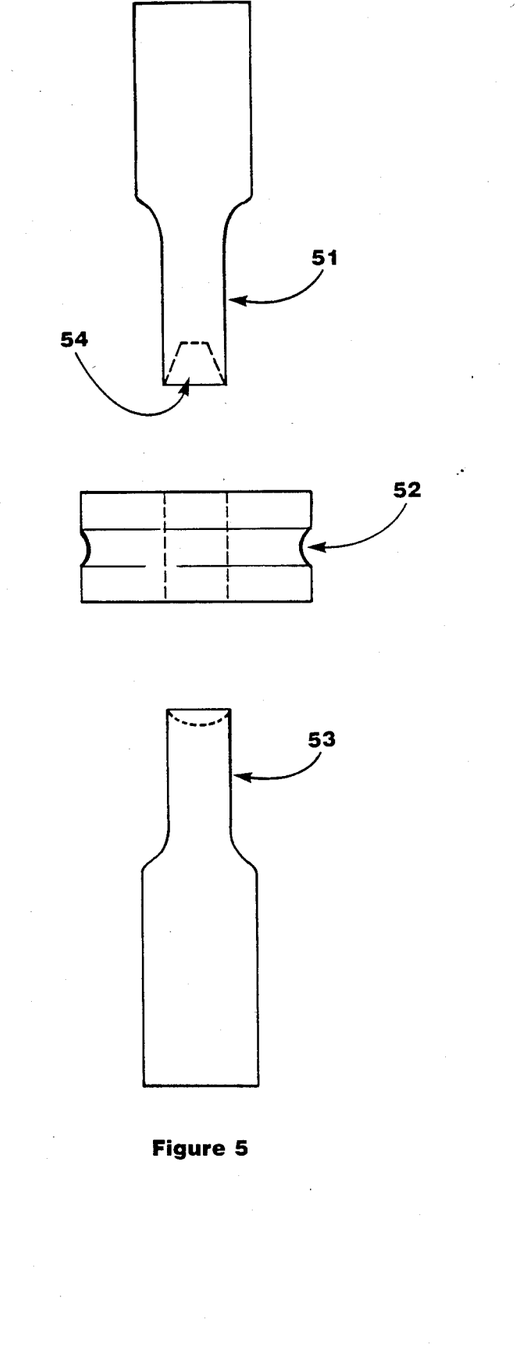
FIG. 5 illustrates the unconventional upper punch, and conventional lower punch and die used in a conventional tablet press for the manufacture of uncoated tablet cores in the shape of a truncated cone.

In said efficient manufacturing process, uncoated tablets are initially formed in the desired shape of a truncated cone on a single or multistation tablet press which is conventional except for the use of an upper punch having a cavity substantially in the shape of a truncated cone. FIG. 5 illustrates in cross-section such an unconventional upper punch 51 having a cavity 54 in the shape of a truncated cone, used in conjunction with a conventional die 52 and lower punch 53, which can be flat or preferably convex, as shown. FIG. 1, representing a finished tablet, can also be used to illustrate the shape of the present punches and die. Thus, in cross-section, the face of the upper punch is represented by a line connecting points CBAHGF, with the cavity designated as 1, while the face of the lower punch in convex form (cavity designated as 3) is represented by the curved line DE. The inside diameter of the die is the straight line DE (or CF), matching the outside diameter of each punch. The punches and die are conventionally manufactured to the desired specifications.

Although powders of active compounds having appropriate physical properties can be tabletted without excipients, the active compound will generally be thoroughly blended with conventional, pharmaceutically acceptable tablet excipients to form either tablets of the dissolution type (where the excipient disintegrates and generally dissolves along with the active ingredient) or of the matrix type (where the active ingredient diffuses into the surrounding medium leaving the matrix intact). Excipients typically used for either purpose are exemplified below.

Figure 3:
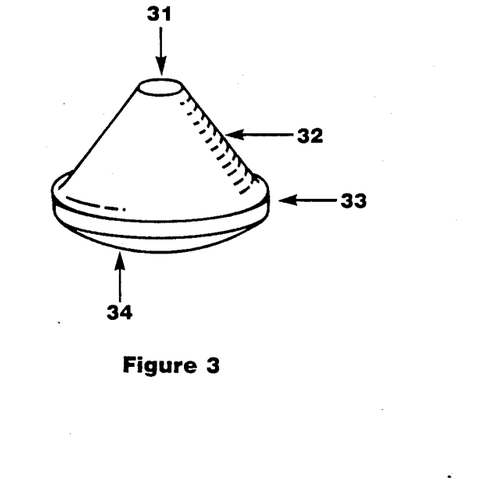
FIG. 3 represents a perspective view of FIG. 1.

Since in standard operation of the tablet press, the upper and lower punches do not touch one another, and each punch will generally have a small flat area at its outer edge, the tablets formed in this manner necessarily possess a flat cylinder or disc shaped central portion, designated as 2 in FIG. 1 and 33 in FIG. 3. The thickness (CD/DF in FIG. 1) of this disc shaped portion can be minimized, e.g., to as little as 0.02 to 0.04 inches, but even if it is relatively thick, e.g. even up to one quarter of the height of the truncated cone, it will not have a significantly adverse effect on the desired zero-order rate of release of the active ingredient.

Figure 2:
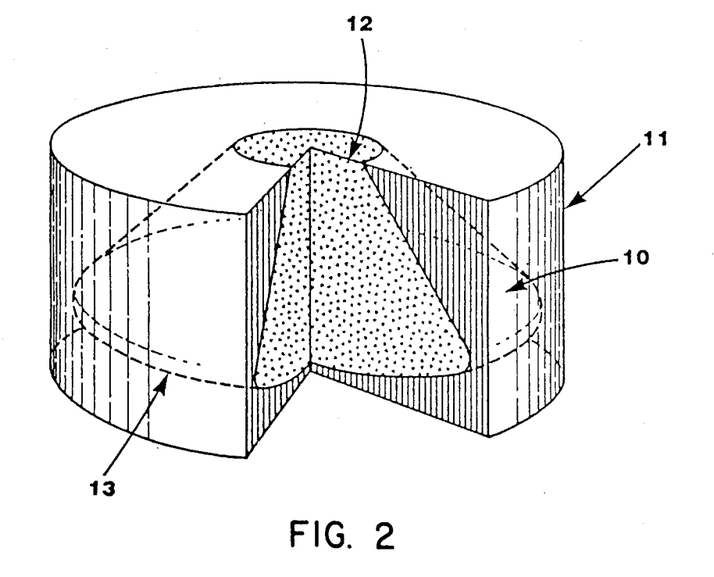
FIG. 2 shows in perspective a segment of a flat cylindrical container with a cavity substantially in the shape of a truncated cone, having a convex base and a circular aperature in the top circular face of the cylinder which is also the top of said cavity. When the device is a tablet, the container is formed by high speed compression coating of a preformed tablet in the shape of a truncated cone. When the device is a bolus such a container can be filled by injecting the active ingredient in melted form.

Once formed the tablets are optionally compression coated by conventional methods (see Ellis et al., Chapter 10, "Tablet Coating", in "The Theory and Practice of Industrial Pharmacy", Lachman et al., eds., Lea and Febiger, 1970, p. 207 et. seq.) to form cylindrical or drum shaped tablets, as illustrated in FIG. 2, where, in segmented perspective, 10 represents the original truncated cone shaped tablet, having a convex base 13 and containing the active ingredient and drug release surface accessing the environment at 12, and the vertically cross-hatched portion refers to the added compression coating 11 having an over-all cylindrical shape.

However, it is preferred at this stage to coat the tablets using conventional methods and materials. See Ellis et al., loc. cit. The coating materials which are used are substantially impermeable to the tablet contents and to the ultimate gastrointestinal fluid. Such conventional materials include aqueous dispersions of ethyl cellulose (e.g. Aquacoats sold by FMC Corp.) which are sprayed onto the tablets and the coating dried in conventional coating pans. On an experimental scale, coating is conveniently accomplished by repeated dipping of the tablet in a volatile organic solution of a polymer such as ethylene-vinyl acetate copolymer and drying. Methylene chloride or toluene are the preferred solvents when the tablet coating is an ethylene-vinyl acetate copolymer.

Figure 6:
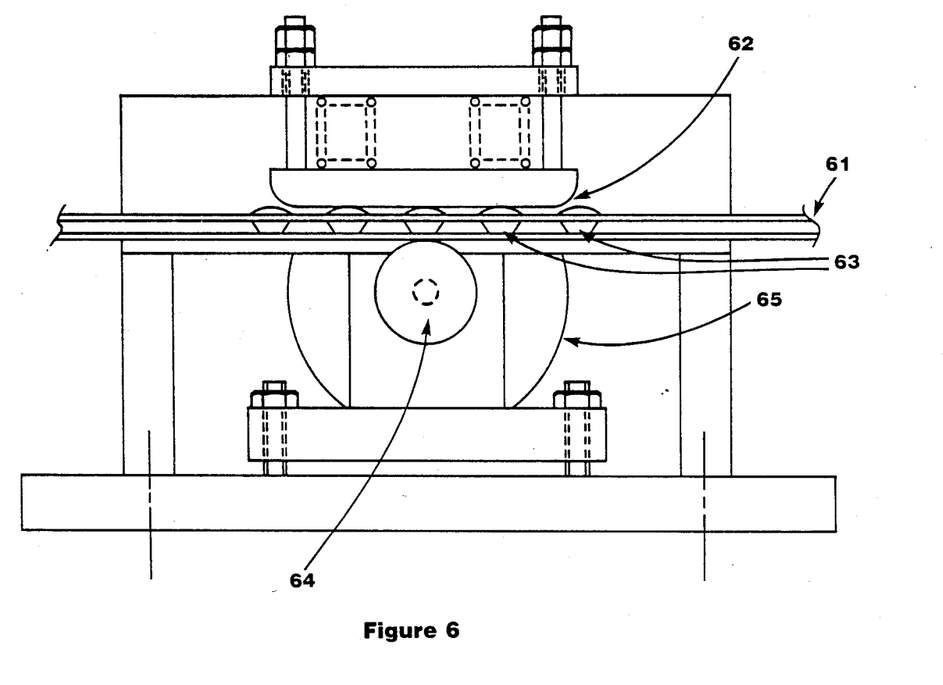
FIG. 6 shows in cross-section a side view and FIG. 7 a view from above of apparatus useful in removing the coating from the top (smaller diameter end) of conventionally coated tablets which are in the shape of a truncated cone.
Figure 7:
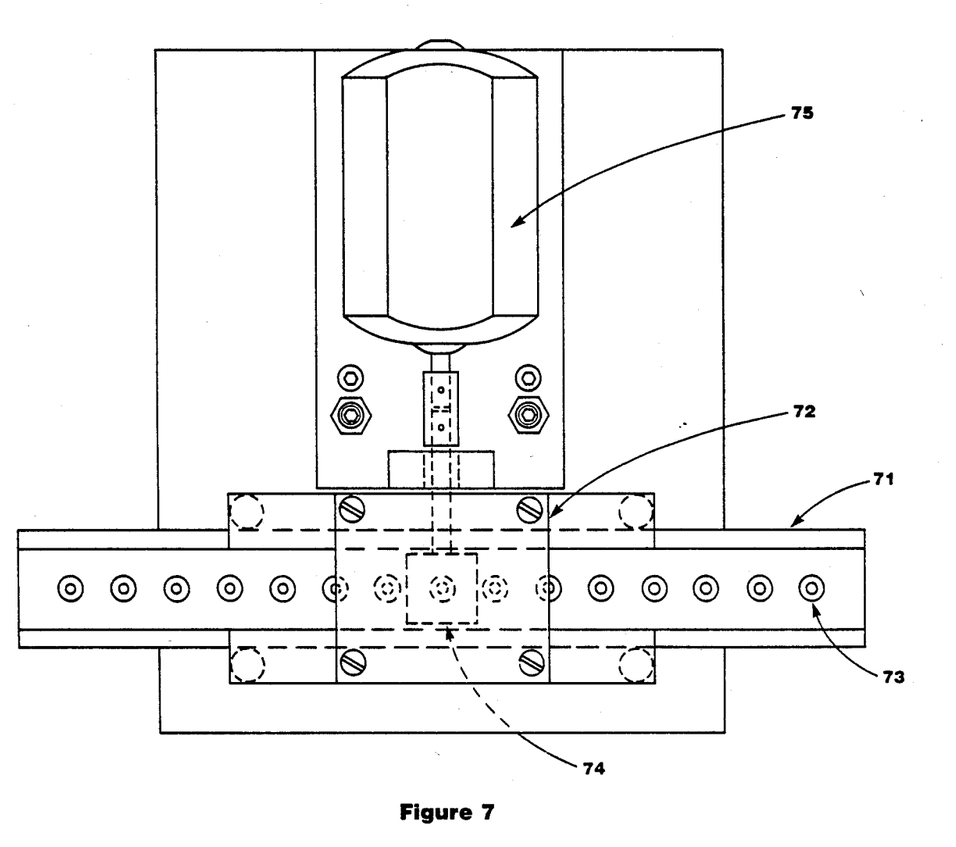

The last stage in the manufacture of present partially coated tablets employs further unconventional apparatus, whose purpose is to remove the impermeable coating from the top (or small end) of the truncated cone, so as to permit ultimate access of the tablet contents to intestinal fluid. Two views of such apparatus, particularly useful for the manufacture of experimental quantities of tablets of the present type, are illustrated in FIGS. 6 and 7, in side and top views, respectively. Tablets 63 are seated in corresponding perforations 73 in the movable plate 61/71. The perforations are also in the shape of truncated cone which is substantially equiangular with the truncated cone of the tablets, but of lesser height. The larger top diameter of the perforations is usually similar to, but not larger than the diameter and the large end of the tablets. The smaller diameter at the bottom of the perforations is larger than the diameter at the small end of the tablets, such that at least some portion of the seated tablets will be below the plane of the plate.

As the plate 61/71 is moved from right to left in FIGS. 6 and 7, the tablets 63 move under and are held in place by the support means 62/72 as they move over the grinding means 64/74 (e.g. a rotary cutting wheel or grinder rotated by a motor 65/75), adjusted so as to remove the coating from the smaller end of each tablet. As the finished tablets move further to the right, they are ejected from the plate.

Figure 8:
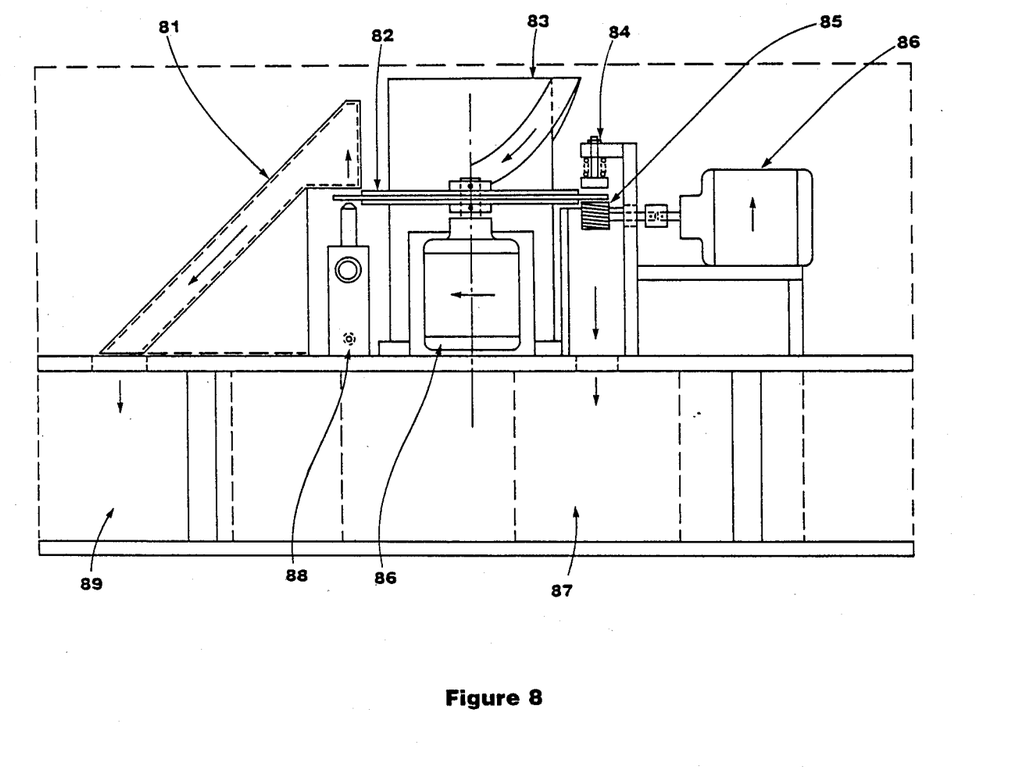
FIGS. 8 and 9 show in side and top views an alternative form of the apparatus useful for removing the top coating from tablets.
Figure 9:
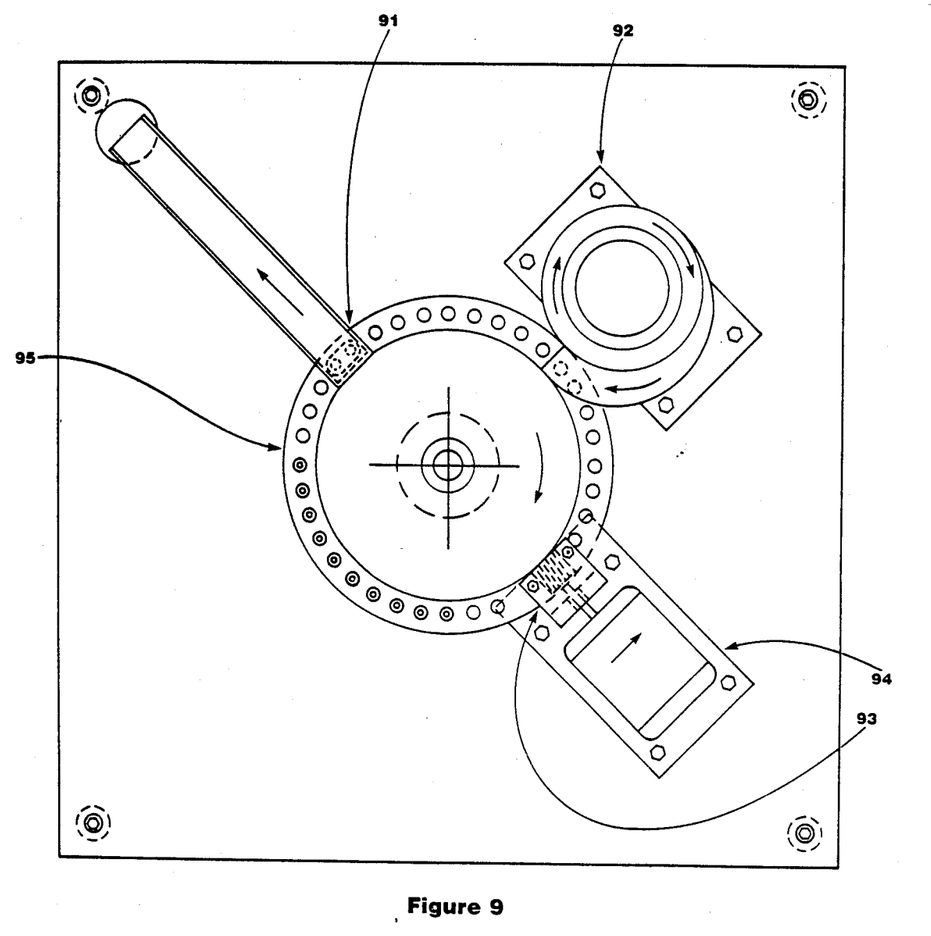

Apparatus for larger scale operation is illustrated in FIGS. 8 and 9, side and top views, respectively. The tablets are held in like perforations in a circular plate 82/95 rotated by an attached variable speed motor 86. The tablets are seated into the like shaped perforations in one segment of the circular plate by vibrational means, e.g., a vibrating bowl feeder 83/92. The support means 84 will permit only those tablets which are seated to move, by rotation of the plate, into the stationary grinding station, comprising a cutter wheel or grinder 85/93 and attached variable speed motor 86/94. Waste powder is collected in a bin 87 below the grinding means. Once finished, the tablets will be ejected in the next segment, e.g., by a combination of a sloping stationary plate mounted below the moving plate which unseats the tablets and a stationary gate, perpendicular to the moving plate and mounted at an angle which sweeps the dismounted, finished tablets into a receptacle; or by an air ejector means 88/91 such that the tablets exit via chute 81 to a receptacle 89.

In order to more dependably achieve a substantially constant tablet to tablet uncoated release area, concave sided tablets or slight tapering of the side at the top the truncated cone of the fully coated tablets prior to removal of the top coating by machine. In this way, any slight tablet to tablet variation in the depth of cut will lead to insignificant variation in the release area.

Finished tablets prepared in this manner are illustrated by FIGS. 1, 3 and 4. FIGS. 1 and 3 represent a tablet in the form of a truncated cone having a convex base and a small cyclindrical section or disc at the base of the cone and a convex base. In FIG. 1, the cross sectional area 1 is the portion of the tablet formed by the upper punch, 2 is the flat disc formed by the die, 3 is the convex base portion formed by the lower punch, 4 is the impermeable coating and 5 is the tablet face from which the coating has been removed. FIG. 3 shows a like tablet in perspective. The tablet coating has been removed from the face 31. The volume 32 is the portion of the tablet formed by the upper punch, 33 is the flat disc formed by the die, and 34 is the convex base formed by the lower punch. FIG. 4 illustrates an alternative embodiment of the tablet in cross section, having coating 41, coating free surface 42, concave shaped side 43 and convex base 44.

The finished tablets are tested in vitro for zero order release of the active ingredient are detailed in the Examples below. The in vitro tests are correlated with the in vivo rate of release, for example by measuring the blood levels of an active agent over time following ingestion of the tablet.

When the present device is used for delivery of active agent(s) to a ruminant mammal it will generally be in the form of a bolus for long term delivery (e.g., 2 weeks or more) in the rumeno-reticular sac (rumen or reticulum) of a ruminant animal, dosed orally by means of a conventional bolling gun. The bolus is designed so that it is of a size that will permit introduction into the rumeno-reticular sac via the esophagus, and retained there by means of its weight, or by means of a change in shape which occurs after its administration.

Figure 10:
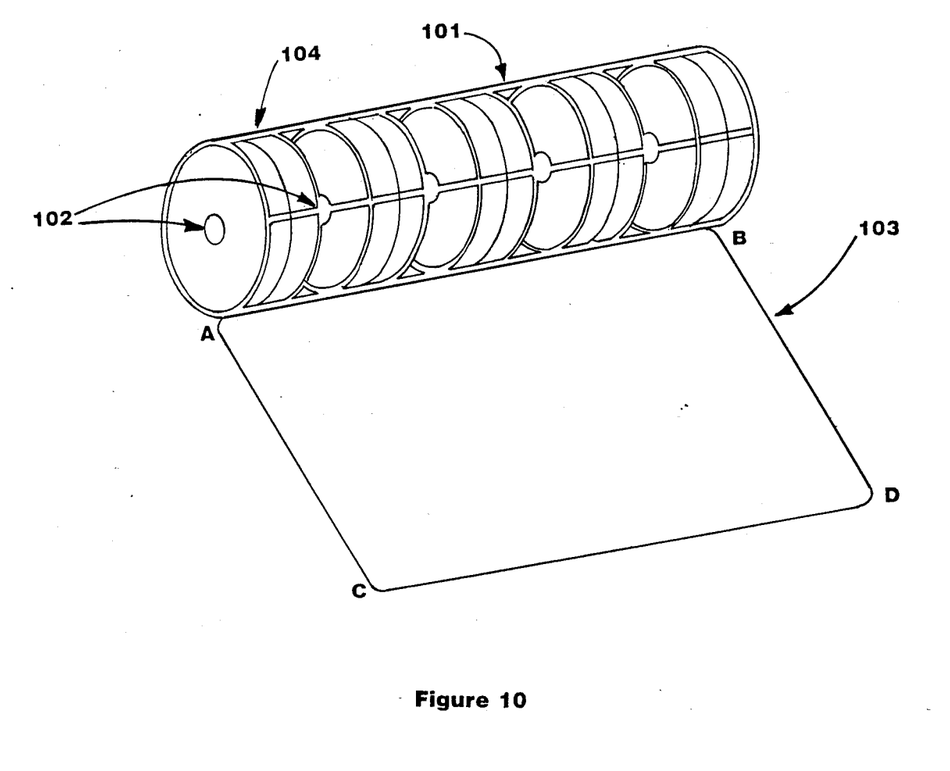
FIG. 10 illustrates in perspective a bolus of the present invention.
Figure 11:
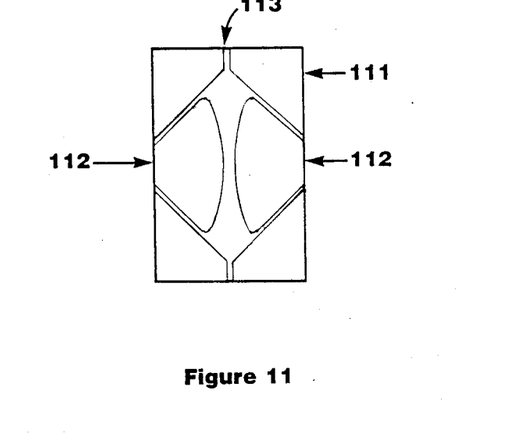
FIG. 11 illustrates in cross-section a back to back pair of flat cylinders or discs which are mounted in a carrier to form the bolus of FIG. 10.

In the present instance, it is convenient to prepare discs or drums containing a cavity substantially in the shape of a truncated cone with ultimate access to the rumeno-reticular environment at the top of a cone as a circular opening in the face of the drum or disc. The active ingredients are homogeneously blended with a meltable polymer powder (for example, the bioerodable p-dioxanon or 65/35 lactide glycolide copolYmer of U.K. Patent No. 2,077,103), the blend melted and injection molded in the desired truncated cone shape. As shown in FIG. 11, the molded drug containing cones are then mounted by means of an adhesive 113 into a cylindrical shaped holder 111, conveniently constructed of moldable plastic, so as to have on opposite faces drug release surfaces 112. Alternatively, preformed discs having a cavity in the shape of a truncated cone, e.g., as illustrated in FIG. 2, are injected with the drug in a meltable polymer, and after cooling and solidification, glued back to back to form a cylinder similar to that shown in FIG. 11 with like drug release surfaces 112 on opposite faces. As shown in FIG. 10, the cylinders or "double discs" 104 having drug release surfaces 102 on opposite faces are mounted into a rack 101 conveniently constructed of moldable plastic or metal. The cylinders are spaced in a manner which permits access of the mixture of active ingredient(s) and polymer to the ultimate rumeno-reticular environment. The rack and mounted discs form an elongated cylinder well suited for introduction into the remeno-reticular sac by means of a bolling gun. The drug release surfaces 112 at each end of the elongated cylinder access the environment directly, and two such surfaces access each space within the elongated cylinder. When the rack is of plastic construction, a rectangular flap 103 is permanently attached by snaps or by means of a water insoluble glue along its edge AB. The rectangular flap, constructed of an insoluble, flexible and resilent material is wrapped in rolled configuration around the elongated cylinder, constrained in that configuration by a constraining means, e.g., attached on the opposite edge CD of the rectangular flap edge with a water soluble glue, e.g., gelatin or a starch or cellulosed based paste. Once orally injected into the rumen or reticlum, the constraining means dissolves, releasing the flap at the, edge CD. The resilent flap then unrolls to provide a substantially flat flap 103 as illustrated, the whole providing a geometric shape and size which retains the device within the rumeno-reticular sac. The flap is suitably constructed of polyethylene or of a thermoplastic elastomer such as a styrene/elastomer block copolymer, or polyurethane and polyester/polyether block copolymers (see "Modern Plastics Encyclopedia 1985–1986, pp. 97–99). Alternatively, the rack is constructed of metal or ceramic so as to have sufficient weight to be retained in the rumeno-reticular sac by meas of gravity, without need for a releasable flap.

The following examples are given by way of illustration and are not to be construed as limitations of this invention, many variations of which are possible within the scope and spirit thereof.

EXAMPLE 1

Dissolution Type Tablets of Sodium Benzoate

Powders of sodium benzoate (30 parts by weight), spray dried lactose (69.5 parts by weight) and magnesium stearate (0.5 parts by weight) were thoroughly blended. By compression means, the blend was compressed into ordinary flat cylindrical tablets having a height of 0.17 inches and a diameter of 0.41 inches. Using an ordinary file, the tablets were filed down into the shape of truncated cones, containing the original height and base dimensions. In this manner, two sizes of tablets were prepared, one having a 0.2 inch top diameter (a top:bottom ratio of 1:2) and weighing 0.34 g., and the other having a 0.14 inch top diameter (a top:bottom ratio of 1:3) and weighing 0.30 g. The tablets were hand coated by repeated dipping of a portion of the tablet into a 10% methylene chloride solution of ethylene-vinyl acetate copolymer (Elvax 40, DuPont, 40% vinyl acetate) and drying. In this case a total of 3 coats were applied to all portions of each tablet. The cross section of coating at the top of each tablet was removed with a razor blade.

Figure 12:
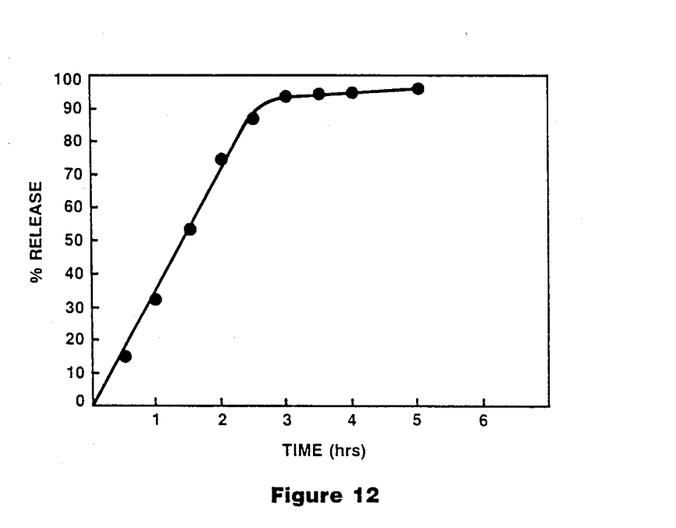
FIGS. 12-16 show the rate of release of active ingredient from tablets prepared in secific Examples below.
Figure 13:
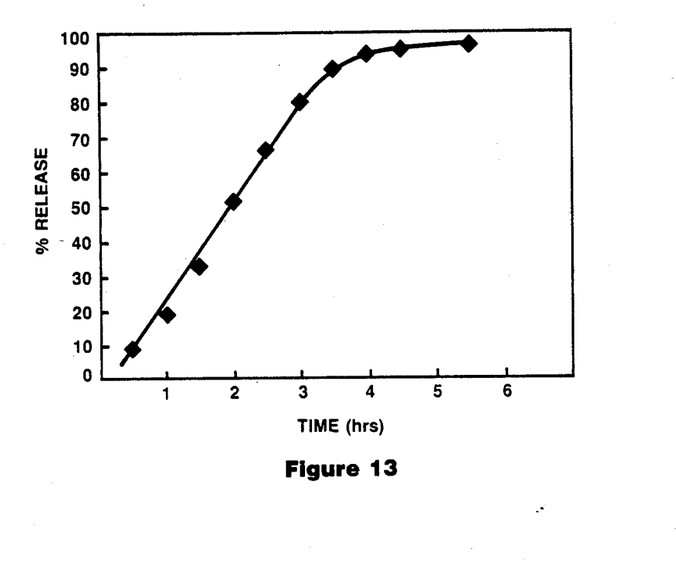

To test the rate of dissolution, simulated intestinal fluid was prepared by dissolving $KH_2PO_4$ (13.6 g.) in 1800 ml. $H_2O$, adjusting the pH to 7.5 with about 16 ml of 5N NaOH, and finally diluting to 2 l. with $H_2O$. The fluid (110 ml.) was measured into each of six 100 ml., clear glass, Wheaton vials. One tablet was added to each vial. The vials were stoppered and held on a laboratory shaker with rubber bands. The vials were rotated at 8 rpm at 24° C. At 0.5 hour intervals, 1 ml. samples were withdrawn from each vial, are replaced with 1 ml. fresh simulated intestinal fluid. At the same time, depletion geometry was monitored by examining individual tablets. The tablet contents gradually eroded from top to the base of the tablet over 6 hours. The results of the present dissolution study with tablets having a 1:2 top:bottom ratio are shown in FIG. 12. The results with the 1:3 top:bottom ratio tablets are shown in FIG. 13.

EXAMPLE 2

Matrix Type Tablets of Sodium Benzoate

Method A

Powders of sodium benzoate (30 parts by weight), ethyl cellulose (40 parts by weight), spray dried lactose (29.5 parts by weight) and magnesium stearate (0.5 parts by weight) were thoroughly blended. By the methods of the preceding Example, like tablets were prepared.

Figure 14:
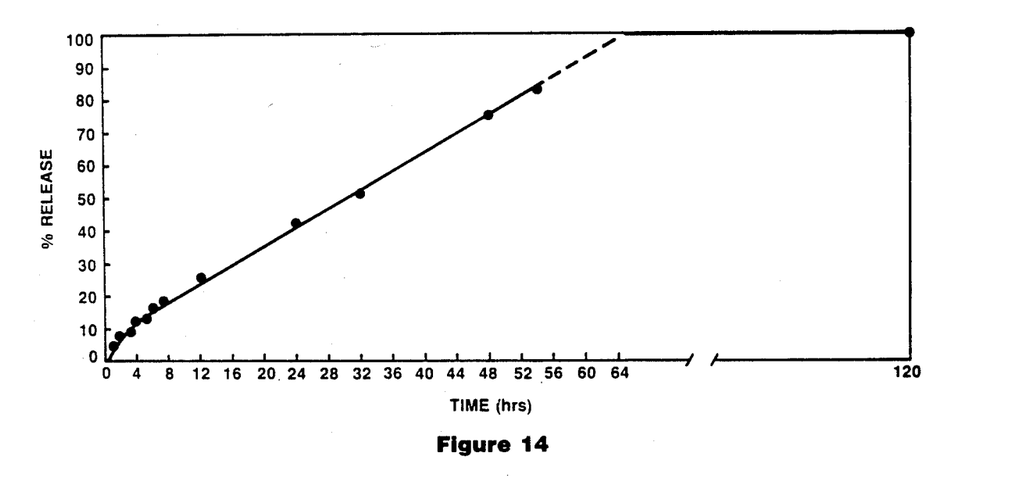
Figure 15:
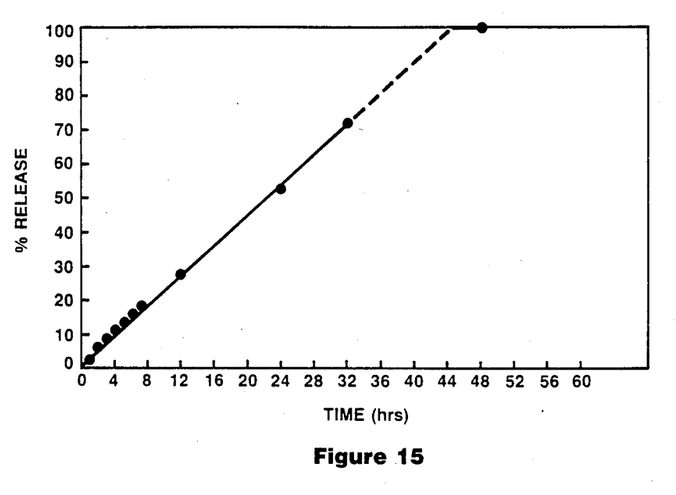

These tablets were tested for rate of dissolution by the method of the preceding Example. Since these tablets were of the matrix type, no erosion of the tablet contents was evident as the sodium benzoate dissolved. The results obtained with present matrix tablets of 1:2 top:bottom ratio are shown in FIG. 14. The results with 1:3 top:bottom ratio are shown in FIG. 15.

Method B

Powders of sodium benzoate (13.80 g., 30 parts by weight), ethyl cellulose (18.40 g., 40 parts by weight), spray dried lactose (12.90 g., 28 parts by weight) were combined in a 250 ml. amber bottle and blended by tumbling for 10 minutes on a Fisher-Kendall mixer. The blend was screened through a U.S.S. Screen #40 sieve and reblended for 5 minutes. Then magnesium stearate (0.90 g., 2 parts by weight) was added and the mixture blended for an additional 5 minutes. The resulting blend was compressed into tablets on a conventional single punch tablet press (Manesty, Model F3) in manual mode, using a specially designed upper punch with truncated cone cavity (as illustrated in FIG. 5, with dimensions corresponding to those of the resulting tablet, as noted below), a conventional die and a conventional round covex lower punch. The average weight of the resulting tablets as 362 mg., containing 108 mg. of sodium benzoate. The tablet dimensions were: top diameter, 0.135 inches; bottom diameter 0.41 inches; over-all height, about 0.23 inches; the flat, cylindrical portion at the base of the truncated cone was 0.04 inches thick. The tablets were readily handled; they were not friable, having a more than acceptable range of tablet hardness (Kp=7.5) when conventionally measured on a Heberlin Hardness Tester. The tablets were coated according to the method of Example 1, except that a toluene was used as the solvent for the copolymer. The coating was removed from the smaller, flat end of the truncated cone by manual operation of the apparatus shown in FIGS. 6 and 7.

Figure 16:
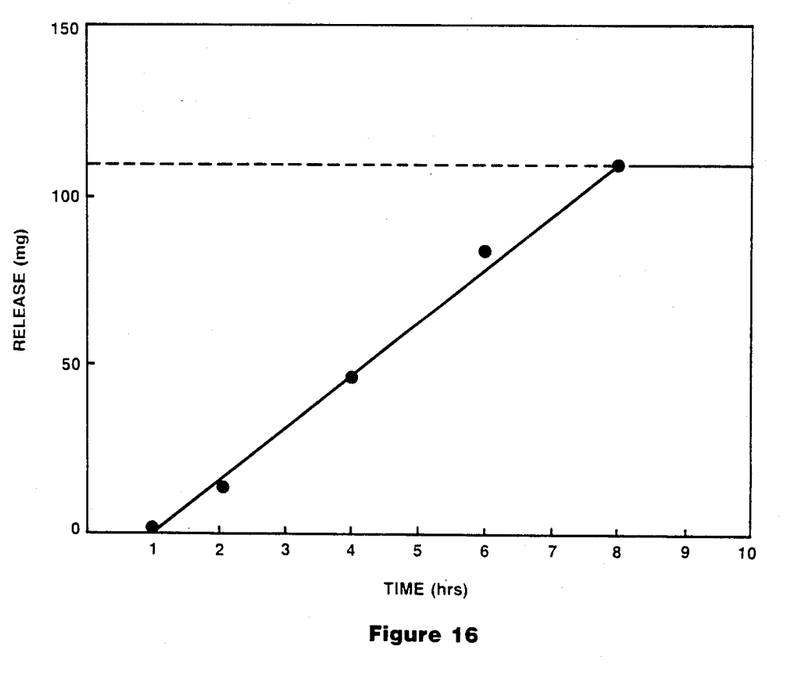

The dissolution of the resulting tablets was studied by the rotating basket method (50 rpm) at 37° C. in 0.01M phosphate buffer at pH 3, otherwise according to the method detailed in Example 1. The results are shown in FIG. 16.

EXAMPLE 4

Trimazosin Tablets

Trimazosin hydrochloride monohydrate (15.50 g., equivalent to 13.80 g., of anhydrous free base), lactose (11.14 g.), ethyl cellulose (18.40 g.) and magnesium stearate (0.90 g.) were blended and formed into tablets according to the preceding Example. The tablets weighed 320 mg., containing 96 mg of trimazosin (free base) activity. They showed an acceptable range of tablet hardness (8–8.5), and were of substantially identical dimensions to those of the preceding Example, except that the thickness of the flat cylinder at the base of the truncated cone was 0.03 inches. The tablets were coated and the flat top removed in the same manner as in the preceding Example.

EXAMPLE 5

Sertraline Tablets

Sertraline HCl (antidepressant, (+)-cis-4-(3,4-dichlorophenyl)-1,2,3,4-tetrahydro-N-metylnaphthylamine; 15.50 g., equivalent to 13.80 g. of free base) and like quantities of the same excipients were converted to tablets according to the preceding Example. The tablets were of like dimensions, except that the disc shaped portion at the base of the truncated cone was 0.05 inches thick. Tablet hardness was acceptable (8.4). The weight of the tablets was 420 mg., corresponding to 126 mg. of sertralne (free base activity).

Controlled release tablets containing the desired activity level of prazosin, doxazosin, hydroxyzine, pirbuterol and glipizide are prepared in like manner.

EXAMPLE 6

Morantel Tartrate Bolus

Powders of morantel tartrate and ethylene vinyl acetate copolymer are blended in the proportion of 55:45 by weight. Suitable copolymer designated MU-760 is available from U.S. Industrial Chemical Co. by injection molding, this mixture is formed into the shape of truncated cones having a convex base, with top diameter 0.23 inch, base diameter 0.7 inch and height 0.41 inch. As illustrated in FIG. 11, each cone is fitted and glued into a flat cylinder or disc (premolded of polyethylene) having a like shaped cavity, and each pair of discs is glued back to back. Five pairs of discs are mounted into a polyethylene rack as shown in FIG. 10, with about 0.3 inch space between each pair of discs. The overall length of the cylindrical rack is about 5.3 inches and the diameter about 1 inch. A rectangular flap, 5.3×4 inches with rounded corners, is cut from 0.03 inch thick high density polyethylene sheet and attached by a 5.3 inch side with water insoluble glue to the cylindrical rack, as shown in FIG. 10. Finally, the flap is wrapped around the cylindrical rack and attached along the other 5.3 side by a tape having a water soluble adhesive. The bolus contains about 4 g. morantel base activity.

In like manner, triple sulfa bolus are preared by substituting the morantel tartrate with 18 parts by weight of sulfamethazine, 18 parts by weight of sulfamerazine and 18 parts by weight of sulfathiazole.

EXAMPLE 7

Diaper Pail Deodorant

A cylindrical container, substantially as illustrated in FIG. 2, having an outside diameter of inches and a height of 2 inches, and truncated cone shaped cavity with 0.8 inch diameter opening at the top, 2.3 inch diameter base and height of 1.4 inches, is constructed of polyethylene by injection molding. A mixture of p-dichlorobenzene and polyethylene glycol (average molecular weight, 1000) in 60:40 portions by weight is melted by warming. The container is filled with the melt, which solidifies on cooling to room temperature, and sealed with paper. The latter is removed prior to use as a deodorant in tne air space of a diaper pail, where it is effective for at least several days to 2 weeks or more.

EXAMPLE 8

Toilet Tank Germicide

The polyethylene container of the preceding Example is filled with a melted mixture of germicidal o-phenylphenol and p-dioxanone in 1:10 ratio by weight. The filled container is cooled and sealed with paper. The paper is removed just prior to use in a toilet tank, where it provides effective germicidal action for several weeks under typical use conditions.

I claim:

1. A device for the controlled release of one or more active substances into a fluid medium which comprises said substance homogeneously disposed, with or without one or more inert diluents, and contained substantially in the shape of a truncated cone by means of an impermeable wall or coating on the base and side of said truncated cone.

2. A device of claim 1 wherein the truncated cone has a convex base.

3. A device of claim 1 wherein the ratio of the diameters of the top to the base of the truncated cone is in the range of 1:2 to 1:4, and the ratio of the height to the diameter of the base is in the range of 1:1 to 1:4.

4. A device of claim 3 wherein the truncated cone has a convex base.

5. A device of claim 2 wherein the truncated cone has a concave side.

6. A device of claim 4 wherein the truncated cone has a concave side.

7. A device of claim 1 wherein the substance is biologically active.

8. A device of claim 7 wherein the activity is to prevent or reduce odors in or emanating from the fluid medium.

9. A device of claim 7 wherein the substance has germicidal activity.

10. A device of claim 7 wherein the substance has pharmaceutical activity.

11. A bolus for oral administration into the reticulum or rumen of a ruminant mammal, said bolus being retained in said rumen or reticulum and releasing one or more active agents into the environment of said rumen or reticulum at a substantially constant rate over a prolonged period of time, which comprises said active agent or agents homogeneously disposed in a matrix and contained substantially in the shape of one or a plurality of truncated cones by means of an impermeable wall on the base and side of said truncated cone or cones.

12. A bolus of claim 11 having said active agent contained in a plurality of truncated cone shaped cavities in a plurality of flat cylinders or discs mounted in a carrier of elongated cylindrical shape and spaced to permit of access of the top of said truncated cones to said environment of the rumen or reticulum, said carrier having an attached flexible and resilient flap capable of constrainment in rolled configuration around said elongated cylinder by a constraining means which releases said flap once in the environment of the reticulum or rumen.

13. A bolus of claim 12 wherein the active agent is morantel or a pharmaceutically acceptable salt thereof in a polymer matrix.

14. A tablet for oral administration to a mammal which releases a pharmaceutically active substance into the fluid of the gastrointestinal tract if said mammal at a substantially constant rate over an appreciable time interval which comprises said substance homogeneously disposed, with or without one or more pharmaceutically-acceptable diluents, and contained, substantially in the shape of a truncated cone, by means of an impermeable coating or wall on the base and side of said truncated cone.

15. A tablet of claim 14 wherein the truncated cone has a convex base.

16. A tablet of claim 14 wherein the ratio of the diameters of top to the bottom of the truncated cone is in the range of 1:2 to 1:4, and the ratio of the height to the diameter of the base is in the range of 1:1 to 1:4.

17. A tablet claim 16 wherein the truncated cone has a convex base.

18. A tablet of claim 15 wherein the truncated cone has a concave side.

19. A tablet of claim 17 wherein the truncated cone has a concave side.

20. A tablet of claim 14 contained by means of coating.

21. A tablet of claim 17 contained by means of coating.

22. A tablet of claim 21 wherein the substance is an antihypertensive.

23. A tablet of claim 22 wherein the substance is prazosin.

24. A tablet of claim 22 wherein the substance is trimazosin.

25. A tablet of claim 22 wherein the substance is doxazosin.

26. A tablet of claim 21 wherein the substance is an antianxiety agent.

27. A tablet of claim 26 wherein the substance is hydroxyzine.

28. A tablet of claim 26 wherein the substance is sertraline.

29. A tablet of claim 21 wherein the substance is a bronchodilator.

30. A tablet of claim 29 wherein the substance is pirbuterol.

31. A tablet of claim 21 wherein the substance is a blood-glucose lowering agent.

32. A tablet of claim 31 wherein the substance is glipizide.

33. A single-station or multistation tablet press for use in the manufacture of tablets substantially in the shape of a truncated cone which, at each station, comprises
    (a) a conventional, substantially round and flat or convex lower punch;
    (b) a conventional, substantially round die; and
    (c) a corresponding upper punch having a cavity which is substantially in the shape of a truncated cone.

34. A tablet press of claim 33 wherein the lower punch is convex.

35. A tablet press of claim 34 wherein the side of the cone shaped cavity is concave in shape.

36. A tablet press of claim 34 wherein the ratio of the diameters of the top and the base of said truncated cone is in the range of 1:2 to 1:4 and the ratio of the height to the diameter of the base is in the range of 1:1 to 1:4.

37. An apparatus for removing the coating from the smaller diameter end of a fully coated tablet which is substantially in the shape of a first truncated cone, which comprises
    (a) a moving, horizontal plate containing a plurality of perforations substantially in the shape of a second equiangular truncated cone of lesser height, having its larger diameter at the top of the plate and no larger than the larger diameter of said first truncated cone, and its smaller diameter at the bottom of the plate and larger than the smaller diameter of said first truncated cone;

(b) a means for seating said fully coated tablets in said perforations;

(c) a stationary support means above said moving plate to hold the seated tablets in place;

(d) a stationary grinding means below the plane of said plate spaced so as to remove the coating from the smaller diameter end of said supported tablets;

(e) a means of ejecting the finished tablets.

38. A process for the preparation of a tablet of claim 20 which comprises the steps of:

(a) forming uncoated tablets substantially in the shape of a truncated cone in a single-station or multistation tablet press comprising a conventional, substantially round and flat or convex lower punch; a conventional, corresponding substantially round central die; and a corresponding upper punch having a cavity which is substantially in the shape of a truncated cone;

(b) fully coating said uncoated tablets with an impermeable coating by conventional means;

(c) removing the coating from the smaller diameter end of the fully coated tablets by means of apparatus comprising a moving horizontal plate having perforations of a shape and size to seat said tablets with the smaller end below the plane of the plate; a means for seating said fully coated tablets in said perforations; a stationary support means above said moving plate to hold said tablets in place; a stationary grinding means below the plane of said plate spaced so as to remove the coating from the smaller diameter end of the fully coated tablets; and a means for ejecting the finished tablets.

39. A process of claim 38 wherein in step (a) the lower punch is convex.

* * * * *